(12) United States Patent
Goldenberg

(10) Patent No.: US 7,731,667 B2
(45) Date of Patent: Jun. 8, 2010

(54) BONE MARROW BIOPSY NEEDLE

(76) Inventor: Alec S. Goldenberg, 157 E. 32$^{nd}$ St., Second Floor, New York, NY (US) 10016

( * ) Notice: Subject to any disclaimer, the term of this patent is extended or adjusted under 35 U.S.C. 154(b) by 0 days.

(21) Appl. No.: 12/198,510

(22) Filed: Aug. 26, 2008

(65) Prior Publication Data
US 2009/0082697 A1    Mar. 26, 2009

Related U.S. Application Data

(60) Provisional application No. 60/969,061, filed on Aug. 30, 2007.

(51) Int. Cl.
*A61B 10/00* (2006.01)
*A61B 17/32* (2006.01)

(52) U.S. Cl. .................. 600/567; 600/562; 600/564; 600/566; 600/568; 606/167; 606/170

(58) Field of Classification Search ............... 600/562, 600/564, 566–568; 606/167, 170
See application file for complete search history.

(56) References Cited

U.S. PATENT DOCUMENTS

| | | | | |
|---|---|---|---|---|
| 3,605,721 A * | 9/1971 | Hallac | .................. | 600/567 |
| 4,262,676 A * | 4/1981 | Jamshidi | .................. | 600/566 |
| 5,074,311 A * | 12/1991 | Hasson | .................. | 600/567 |
| 5,522,398 A * | 6/1996 | Goldenberg et al. | .................. | 600/567 |
| 5,634,473 A * | 6/1997 | Goldenberg et al. | .................. | 600/567 |
| 6,015,391 A * | 1/2000 | Rishton et al. | .................. | 600/567 |
| 6,471,709 B1 * | 10/2002 | Fawzi et al. | .................. | 600/562 |
| 7,278,970 B2 * | 10/2007 | Goldenberg | .................. | 600/564 |
| 7,338,456 B2 * | 3/2008 | Goldenberg | .................. | 600/564 |
| 7,384,400 B2 * | 6/2008 | Goldenberg | .................. | 600/564 |
| 7,455,645 B2 * | 11/2008 | Goldenberg | .................. | 600/564 |
| 7,608,049 B2 * | 10/2009 | Goldenberg | .................. | 600/564 |
| 7,621,923 B2 * | 11/2009 | Goldenberg | .................. | 606/159 |
| 2007/0142744 A1 * | 6/2007 | Provencher | .................. | 600/562 |
| 2007/0219460 A1 * | 9/2007 | Goldenberg | .................. | 600/566 |

\* cited by examiner

*Primary Examiner*—Max Hindenburg
*Assistant Examiner*—Emily M Lloyd
(74) *Attorney, Agent, or Firm*—Leason Ellis LLP

(57) ABSTRACT

A biopsy needle for removal of tissue from a patient including an outer tube; an inner tube within the outer tube; and a snare connected to the inner tube and to the outer tube. The outer tube has an outer surface that has a first region that terminates in the distal end and is the distalmost section of the outer tube and a second region adjacent the first region. The first region represents a tip transition region and has a frustoconical shape that is defined by an outer surface area (A) and is defined by a cross-sectional area (Ba) at the interface between the first and second regions in a direction that is perpendicular to the longitudinal axis of the needle, the interface representing a base of the frustoconical first region, wherein a ratio R=(A)/(Ba) is approximately 1 for a predetermined needle type, such as an 8 gauge needle.

16 Claims, 6 Drawing Sheets

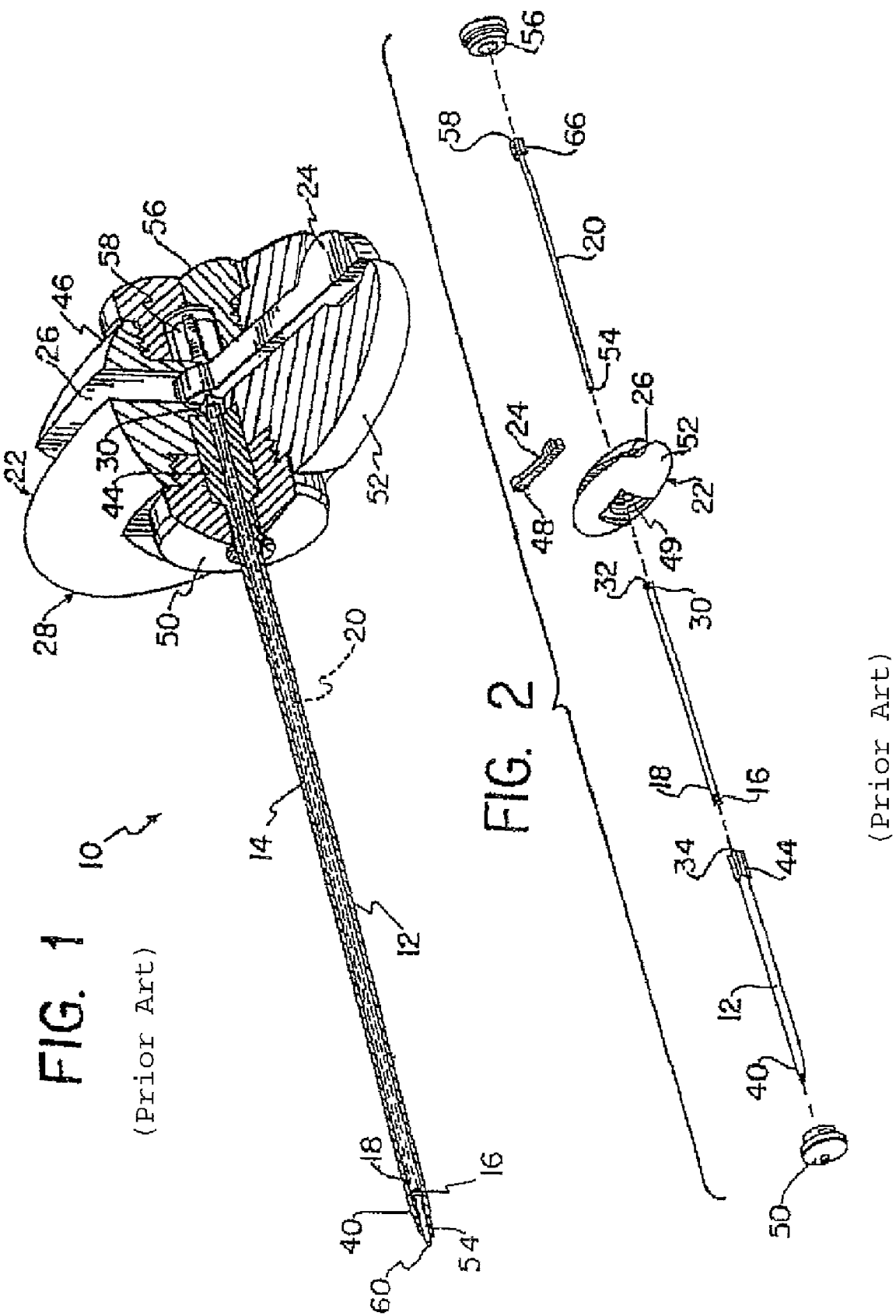

BONE MARROW BIOPSY NEEDLE

CROSS-REFERENCE TO RELATED APPLICATION

The present application claims the benefit of U.S. provisional patent application No. 60/969,061, filed Aug. 30, 2007, which is hereby incorporated by reference in its entirety.

TECHNICAL FIELD

This invention relates generally to a surgical instrument, known variously as a biopsy needle or cannula that is used to gather tissue, such as bone marrow, from living persons or animals for pathological study. More specifically, the invention relates to a biopsy needle having an improved structure for severing a tissue sample and/or retaining the tissue sample within the needle.

BACKGROUND

For various medical reasons, such as evaluating the histology and/or pathology of a tissue, it is often necessary for a physician to obtain a sample of a patient's body tissue. In particular, bone marrow is frequently retrieved to study its cellularity and potential infiltration with abnormal cells. The currently available procedures and instruments used for obtaining bone marrow biopsy samples, while not overly complex, almost universally result in excessive patient discomfort and often recover inadequate quantities of biopsy material which sometimes is distorted and/or difficult to interpret. In the standard bone marrow procurement protocol, using currently available instruments, (such as those disclosed in U.S. Pat. No. 4,262,676 to Khosrow Jamshidi), the patient is prepared with a suitable local anesthetic at the posterior superior iliac crest/spine. Then, a relatively narrow needle is inserted to obtain an aspirate of liquid bone marrow material to make slides for examination of cellular morphology and to evaluate the surface immunophenotype of the bone marrow cells with flowcytometry. This portion of the procedure, referred to as the bone marrow aspiration, is generally relatively less painful than the bone marrow biopsy procedure using a conventional biopsy needle. Using newer bone marrow biopsy needles which actively capture specimens, and minimize manipulation of the needle after insertion, the aspirate procedure appears to be more painful than the biopsy procedure.

After the aspirate is obtained, if necessary, a biopsy of the bone marrow is taken. A significantly wider bore needle having an inner diameter that will accommodate a suitable marrow sample is prepared with an inner stylet that extends beyond the distal end of the outer needle. The stylet's distal end may be cut at an angle, with the leading edge sufficiently sharp to pierce tissue and bone. With the stylet in place within the outer needle, the needle is pushed through the outer layers of skin and subcutaneous tissue until the needle tip reaches the surface of the cortical bone. The needle and stylet are then pushed into and through the cortical layer until the tip has penetrated into the bone marrow space.

The stylet is then removed from the proximal end of the needle, which opens up the core of the needle to accommodate entry of bone marrow material for collection and retrieval. The needle is then usually advanced another 1 to 2 centimeters at minimum with a slight twisting motion. Often, the distal end of the needle will also be provided with an angled cut and sharpened leading edge to facilitate cutting and coring the tissue. By providing a slight twisting motion as the needle is advanced, usually with no more than quarter or half turns, an appropriate sample is cored from the marrow tissue and enters the inner passage of the marrow needle.

At this point, the marrow biopsy sample is ready to be removed from the patient, although it is important that the biopsy remain within the needle as the needle is withdrawn to ensure recovery of the specimen. If the biopsy becomes dislodged and falls through the distal end of the biopsy needle, the specimen is irretrievably lost. The procedure is then unsuccessful and must be repeated from the beginning.

Various methods have been utilized by physicians to try to prevent the biopsy specimen from dislodging from the needle. For example, after the needle has entered the bone and fully cored a sample from the marrow, some physicians, will pull the biopsy needle back a few millimeters and then advance it a few millimeters at a different angle than the first insertion. This theoretically will "cut" the biopsy piece at the tip of the needle. Other physicians attempt to dislodge or disrupt the connection between the specimen and the bone by making multiple complete clockwise and counterclockwise rotations of the biopsy needle while within the bone. Some physicians even hit the proximal end of the biopsy needle at its handle in an attempt to mechanically disrupt the connection between the specimen and the additional bone.

As can be plainly realized, these manipulations at the end of the procedure, attempts at ensuring that the specimen remains within the needle, can often produce substantial discomfort and anxiety to the patient. Sometimes when the bone marrow is very soft, as in patients with osteoporosis, almost all of these attempts are futile because the bone structure is so fragile. Conversely, sometimes when the bone marrow is very fibrotic, which occurs in patients with myelofibrotic diseases or in AIDS patients, it is difficult to dislodge the core biopsy, since the bone marrow itself is reinforced by the surrounding tissue. In those cases, the cored biopsy often remains attached to the bone and is not successfully recovered.

Other attempts at designing a more efficient and successful biopsy needle have met with little or no success, for various reasons, including the complexity of the devices. For example, U.S. Pat. No. 3,605,721 to Hallac, discloses a biopsy needle in which an inner tube has a weakened portion represented by strips extending between distal and proximal portions of the inner tube. The distal portion of the inner tube is adhered to an outer tube and will not rotate. Once a biopsy has entered the needle, the proximal portion of the inner tube is rotated, causing the strips to twist together and eventually break off. This twisting motion tends to twist the strips to the tube's center, thus hopefully keeping the biopsy piece proximal of the twisted and broken strips for later removal. This particular biopsy needle is only a disposable device, since the strips are broken or irreversibly warped by deformation during the twisting process. Another disadvantage is the lack of control over the twisting motions or the breakage of the strips. Essentially, the operator is left to twist the inner tube until resistance to that twisting is lost, indicating that the strips have severed. There is also no way of releasing the device's grip on tissue during the procedure, should any problems arise.

U.S. Pat. No. 5,074,311 to Hasson discloses a biopsy device that includes a pair of inner jaws that can be actuated within the outer needle to "bite off" any biopsy piece that has entered the needle. The disadvantages of this device include multiple small mechanical linkages and parts including pivot pins, which are extremely difficult and expensive to assemble and maintain, in addition to the greatly increased chance of mechanical failure resulting in failure to retrieve an adequate specimen.

U.S. Pat. No. 5,522,398, to Goldenberg et al., discloses a bone marrow biopsy needle that offers improvements over the prior art devices. However, in some applications and patients, greater forces are required to penetrate the bone in order to acquire the sample and these forces can present difficulties for some users and to the integrity of the needle. A force is needed to initially anchor the needle which is the process of penetrating the bone before the needle is advanced further into the bone marrow space. It therefore would be advantageous to construct an improved needle that offers all the advantages of the previous Goldbenberg snarecoil needles yet provides an improved needle construction that makes it easier for the user to initially anchor the needle in the bone and then advance the needle into the bone marrow space.

SUMMARY

A biopsy needle for removal of tissue from a patient including an outer tube having a distal end; an inner tube within said outer tube; and a snare having a first proximal end connected to the inner tube and a second distal end coupled to the outer tube. The snare has a variable diameter that is controlled by rotation of the inner tube with respect to the outer tube in a prescribed direction resulting in the opening and closing, respectively, of the snare. The outer tube has an outer surface that has a first region that terminates in the distal end and is the distalmost section of the outer tube and a second region adjacent to the first region. The first region represents a tip transition region and has a frustoconical shape that is defined by an outer surface area (A) and by a cross-sectional area (Ba) at the interface between the first and second regions in a direction that is perpendicular to the longitudinal axis of the needle, the interface representing a base of the frustoconical first region, wherein a ratio R=(A)/(Ba) is approximately 1 for a predetermined needle type, such as an 8 gauge needle.

The applicant has discovered that the characteristics of the tip transition region (i.e., the frustoconical section) and the degree of taper in the second region adjacent to the tip transition region influences the degree of force that is required to initially anchor the needle and to advance the needle into the bone marrow space. In particular, the applicant has discovered that there is a relationship between (A) and (Ba) as defined above, and needles having the above ratio value offer improved performance and provide reduced needle penetration forces.

In another embodiment, the distalmost section of the needle is defined by a distalmost section of the inner tube that is attached to the outer tube. In this embodiment, a portion of the inner tube is located distal to the snare and is connected thereto. In this embodiment, a distalmost portion of the outer tube is eliminated (e.g., ground away) so as to expose the underlying distalmost portion of the inner tube, thereby causing the distalmost section of the inner tube to be the distalmost section of the needle. In this embodiment, the first region that represents the tip transition region can be defined by the composite of the exposed distalmost section of the inner tube and the adjacent distalmost section of the outer tube.

BRIEF DESCRIPTION OF THE DRAWINGS

Other objects, advantages and embodiments than those described above will become apparent to those skilled in the art upon reading the following detailed description of the preferred embodiments in conjunction with a review of the appended drawings, in which:

FIG. 1 is a perspective view of a biopsy needle;

FIG. 2 is an exploded view of the biopsy needle of FIG. 1;

DETAILED DESCRIPTION OF THE PREFERRED EMBODIMENTS

Figure 3A:
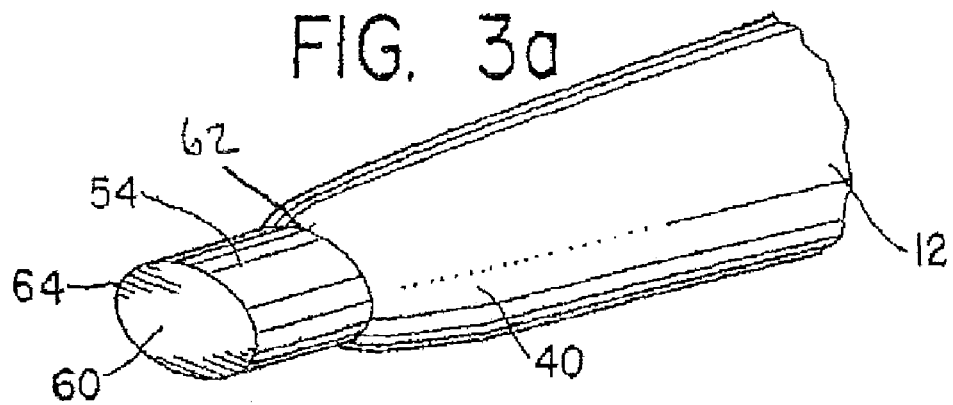
FIGS. 3a-3e are detail perspective views of the distal ends of various components during operation of the biopsy needle.

Referring now to FIGS. 1 and 2, a biopsy needle, according to one embodiment of the present invention, 10 has an outer cannula 12, an inner tube 14 with a snare 16 at its distal end 18, a stylet 20, and a handle assembly 22. In FIG. 2, the assembly of the present biopsy needle 10 is shown in an exploded view. This type of biopsy needle is the subject of a number of applications of the present applicant and in particular, the general construction of the biopsy needle 10 is described in detail in U.S. patent application Ser. No. 11/416,451 (now issued as U.S. Pat. No. 7,338,456); Ser. No. 11/742,333 (now issued as U.S. Pat. No. 7,384,400); Ser. Nos. 11/678,478; and 10/901,917 (now issued as U.S. Pat No. 7,278,970), which are hereby incorporated by reference in their entirety. However, the needle 10 can have any number of other configurations not shown in the above references so long as the needle includes a double lumen snarecoil design in that it includes outer tube 12, inner tube 14 and snare 16 connected therebetween.

As part of the handle assembly 22, a lever 24 fits into a corresponding groove 26 within a handle piece 28. The lever 24 actuates the snare 16 within the outer cannula 12 without any movement of the outer cannula 12 relative to the patient (not shown). The functioning of this lever 24 is described more fully below. The inner tube 14 has a snare 16 at its distal end 18 and a gear or lever connector 30 mounted on its proximal end 32. The inner tube 14 is inserted into the proximal end 34 of the outer cannula 12 with the gear or lever connector 30 extending out of the proximal end 34, which facilitates connection of the lever to the inner tube and uniform conversion of lever rotation to inner tube rotation.

With the gear or connector 30 extending proximal of the outer cannula's anchor 44, the cannula and snare assembly are attached to the handle piece 28 at the distal facing side 52 of the handle 22. The gear 30 of the inner tube 14 is inserted into a complementary hole 48 in the lever while the anchor 44 of the outer cannula 12 mates with a complementary hole 49 in the handle piece 28. Thus, when the lever 24 is rotated within its groove 26 with respect to the handle piece 28, the inner tube 14 will rotate with respect to the outer cannula 12. A cannula cap 50 is assembled onto the distal tip 40 of the cannula and threadingly engaged to the forward facing end 52 of the handle piece 28. In other embodiments, a non-threaded cannula cap or similar retaining member can be bonded to the forward facing end 52 of the handle piece 28 to ensure that the outer cannula 12 does not rotate or move longitudinally relative to the handle 28. The stylet 20 is inserted into the proximal end 32 of the inner tube until a distal tip portion 54 of the stylet extends beyond the distal tip 40 of the cannula. A stylet cap 56 can then be threadingly engaged to the proximal facing side 46 of the handle piece, covering the proximal end 58 of the stylet to prevent it from moving proximally within the inner tube 14. Other embodiments not requiring a stylet cap in which the proximal end of the stylet reversibly connects to the handle to prevent it from moving proximally are possible.

As can be seen in FIG. 3a, both the distal ends 54, 40 of the stylet and the outer cannula of a conventional needle typically have sloped end faces 60, 62 This improves the cutting actions of the both the stylet and the outer cannula by providing sharp leading edges 64. In this position, the stop 66 at the proximal end 58 of the stylet preferably mates with a complementary indent in the handle piece 28 to maintain the rotational orientation of the stylet 20 with respect to the outer cannula 12 such that the slopes of the two distal ends 40, 54 are approximately parallel, or aligned optimally to result in an efficient piercing and cutting action and the stylet does not rotate relative to the outer cannula during the initial bone penetration. This is the configuration that would be used for initiating insertion of the biopsy needle 10 into the bony cortex.

Figure 3B:
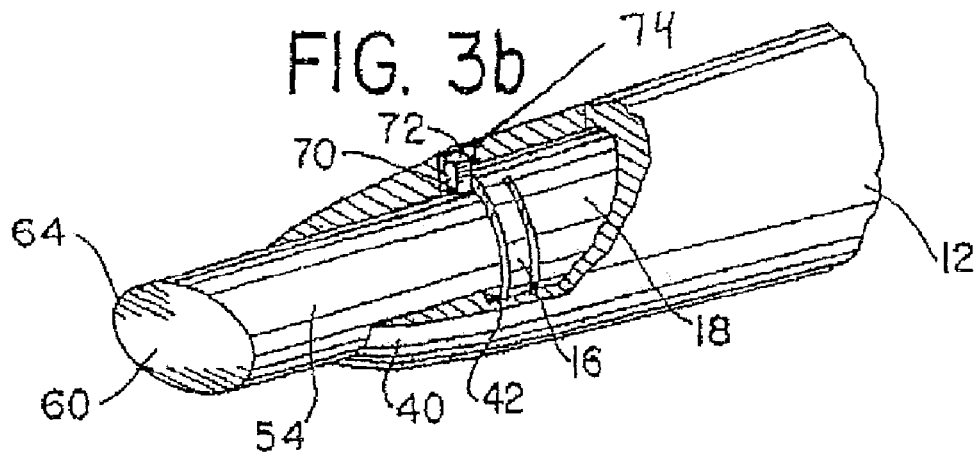

As can be seen in FIG. 3b, which is a partial cutaay view, the free end 70 of the coil snare 16 includes a tab 72 that engages or is attached to a hole 74 on the interior surface of the outer cannula 12. This hole 74 preferably extends through the entire wall of the outer cannula. If desired, the tab 72 can be adhered to the hole 74 in the outer cannula through the use of adhesives, welding, or any known attachment process. However, it will be appreciated that the tab 72 and hole 74 can be eliminated and the outer surface of the inner tube can be bonded to the inner surface of the outer tube by welding or some other type of attachment method. It will therefore be appreciated that so long as the two structures are attached to one another, any number of different techniques can be used to accomplish such a coupling action, including the illustrated manner or using a direct bond between two surfaces, etc.

Figure 3C:
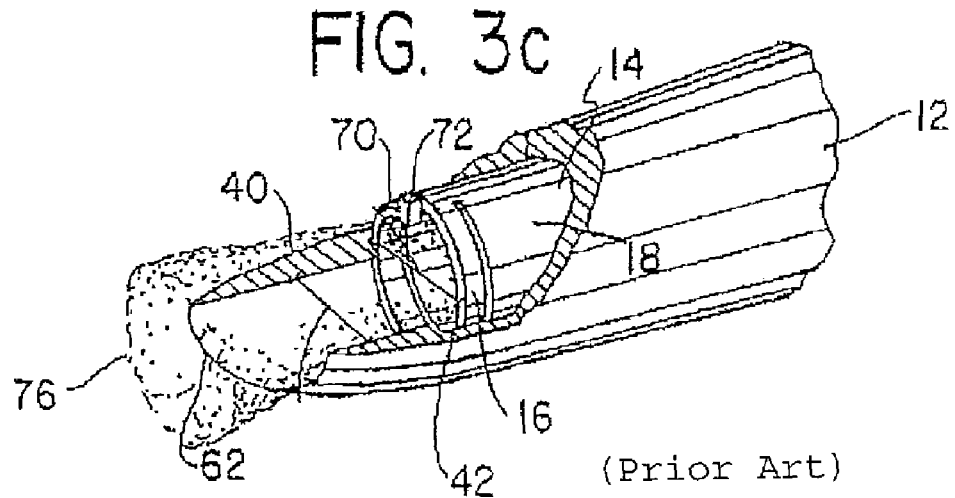

After the needle 10 is inserted into the marrow, the stylet 20 is removed proximally without any movement of the outer cannula 12 with respect to the patient, minimizing discomfort. As can be seen in FIG. 3c, marrow tissue 76 may now enter the passageway within the outer cannula 12 through the distal end 40 of the outer cannula as the needle is advanced further and can enter the inner passageway of the inner tube 14, preferably to a position proximal of the snare 16.

Figure 3D:
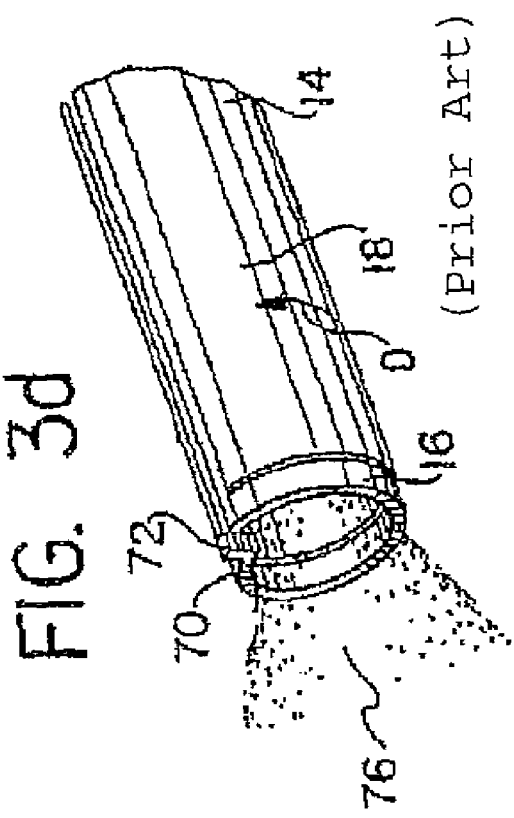
Figure 3E:
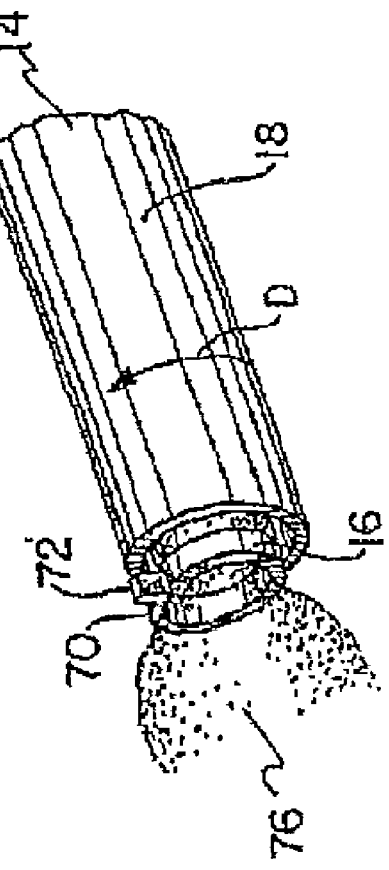

To operate the snare 16, i.e. to cause cutting and/or holding of the biopsy piece 76 within the inner tube 14, the lever 24 attached to the proximal end 32 of the inner tube is rotated in the direction of arrow D as seen in FIGS. 3d-3e. Of course, the snare 16 can be designed such that rotation in the opposite direction causes the same effect. With full rotation (180 degrees) of the lever 24, the inner tube 14 and snare 16 achieve a position similar to that shown in FIG. 3e, in which the inner tube 14 has been rotated approximately 180 degrees. Since the free distal end 70 of the snare is fixed to the outer cannula 12, the result of the rotation is that the coil of the snare 16 will tighten so that the cross-sectional area through the snare 16 is approximately less than a third of the area when in the open configuration. It is also contemplated that any decrease, even a slight decrease, in the cross-sectional area of the snare will cause pressure on the biopsy piece 76. Therefore, while the current amount of rotation is preferred, it is not necessary for the proper functioning of the present invention.

Once the biopsy needle 10 has captured a cored specimen, it must be recovered for pathologic interpretation. The lever is rotated opposite to the direction D, thereby opening up the coil to its original diameter. An obturator is placed through the tip of the needle and the specimen is pushed through the inner tube and through the handle for collection. Once the specimen has been ejected and recovered, the biopsy needle 10 is then ready to be sterilized for its next use. If necessary, the entire biopsy needle can be disassembled, although the tab 72 at the free end of the snare must be disengaged from the hole 74 in the outer cannula. This can be accomplished with any small tool pushed through hole 74. If the free end 70 of the snare is permanently adhered to the outer cannula 12, it then may be necessary to sterilize the outer cannula and inner tube as a single unit. However, due to the few number of parts and relative ease and low cost of construction of the present needle, it is also contemplated that such a device is easily disposable.

In accordance with the present invention, the applicant has discovered that the construction and configuration of the needle 10, and in particular, the outer cannula 12 thereof, influences the amount of force required for needle penetration. FIGS. 1-3 show a general needle shape that is described in the applicant's previous patents and patent applications and while, the needle 10 performs admirably, there is a desire to improve the needle performance by decreasing the amount of penetration force needed to advance the needle into dense materials, such as bone.

Figure 4:
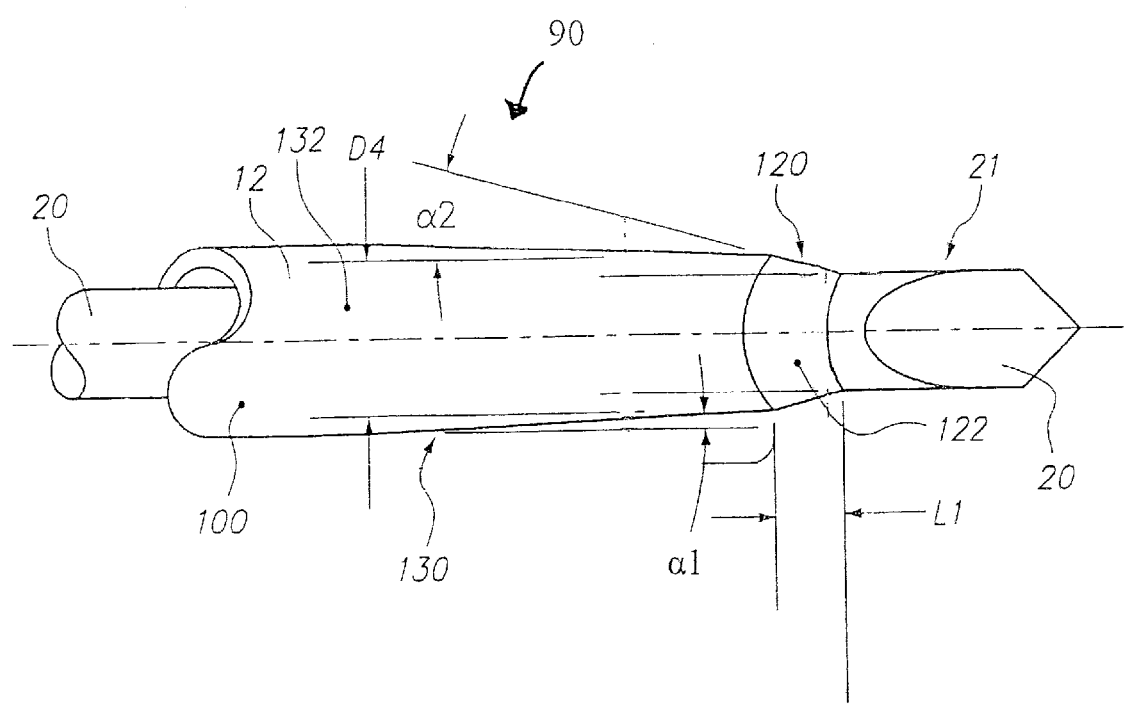
FIG. 4 is a side elevation view of a portion of an outer cannula that is a part of a biopsy needle according to one embodiment of the present invention.

As seen in FIG. 4, a needle 90 that is similar to the needle 10 is shown and includes the outer cannula 12 that has an outer surface 100 that has distinct regions that have different constructions (e.g., different surface characteristics). For purpose of illustration only, the inner tube is not shown in FIG. 4 in order to more clearly show the outer cannula 12 and the features of the present invention. FIG. 4 does show the stylet 20 positioned relative to the outer cannula 12. In particular, the stylet 20 is shown in an advanced position extending beyond the distal end of the outer cannula 12.

The stylet 20 includes a distal end region 21 which is the portion of the stylet 20 that extends beyond the distal end of the outer cannula 12. The outer cannula 12 includes a number of different body sections including a distal region 120 that terminates at the distal end of the outer cannula 12 and represents the most distal aspect of the tip of the outer cannula 12. The outer cannula 12 also includes a second region 130 that is adjacent the distal region 120 and represents a more proximal aspect of the outer surface 100. The second region 130 is a distal portion of a body region of the outer cannula 12 that extends from the proximal aspect of the distal region 120 to the proximal end of the outer cannula 12. As explained below, the second region 130 has a slight taper according to angle a1 and represents a section of a more gradual taper that is located next to the more abrupt taper of the tip transition region (distal region) 120. The gradual taper of region 130 further decreases the resistance of penetration during needle insertion.

This distal region 120 can likewise be properly characterized as being an additional transition region due to it having a relatively abrupt change in shape and contour compared to the adjacent needle region, namely the second region 130 and relative to the more proximal body portion of the outer cannula 12. An outer surface 122 of the distal region 120 geometrically speaking defines a lateral surface area of the needle tip transition region and this outer surface 122 can be expressed in terms of being a tip transition surface area ($TT_{sa}$). As described below, the outer surface 122 of the distal region 120 is a tapered surface.

It will be appreciated that the second region 130 also has an outer surface contour and similar to the distal region 120, although to a much lesser extent, an outer surface 132 of the second region 130 is tapered. This tapered outer surface 132 can be referred to as being the needle taper of the body of the outer cannula 12. An angle α2 that defines the tip transition surface area ($TT_{sa}$) relative to the axial dimension of the outer cannula 12 is greater than an angle α1 that defines the needle taper relative to the axial dimension of the needle (outer cannula 12). The dimension L1 is the height (h) of the frustoconical section (distal region) 120 as measured along the longitudinal axis of the needle 90.

The applicant has discovered that the characteristics of the tip transition region (outer surface 122) and the tapered outer surface 132 (needle taper) influences the degree of force that is required to initially anchor the needle 90 and to advance the needle 90 into the bone marrow space. Differences in the characteristics of both these surfaces 122, 132 and especially, in the distal region 120 results in either an increase or decrease in the force required to penetrate a dense material, such as bone, in order to acquire a sample.

The tapered outer surface 122 of the tip transition region (distal region) 120 can be described as having a frustoconical design as defined from the distal end of the outer cannula 12 to the interface between the tip transition region (distal region) 120 and the second region (body transition region) 130. In other words, the surface area 122 has the shape of a truncated cone and its surface area can be defined using geometrical surface area equations. The frustoconical surface area does not include the top and bottom of the frustoconical shape but instead merely is the surface area of the outer surface 122 and as mentioned above, this surface area can be described as the tip transition surface area ($TT_{sa}$).

Figure 4A:
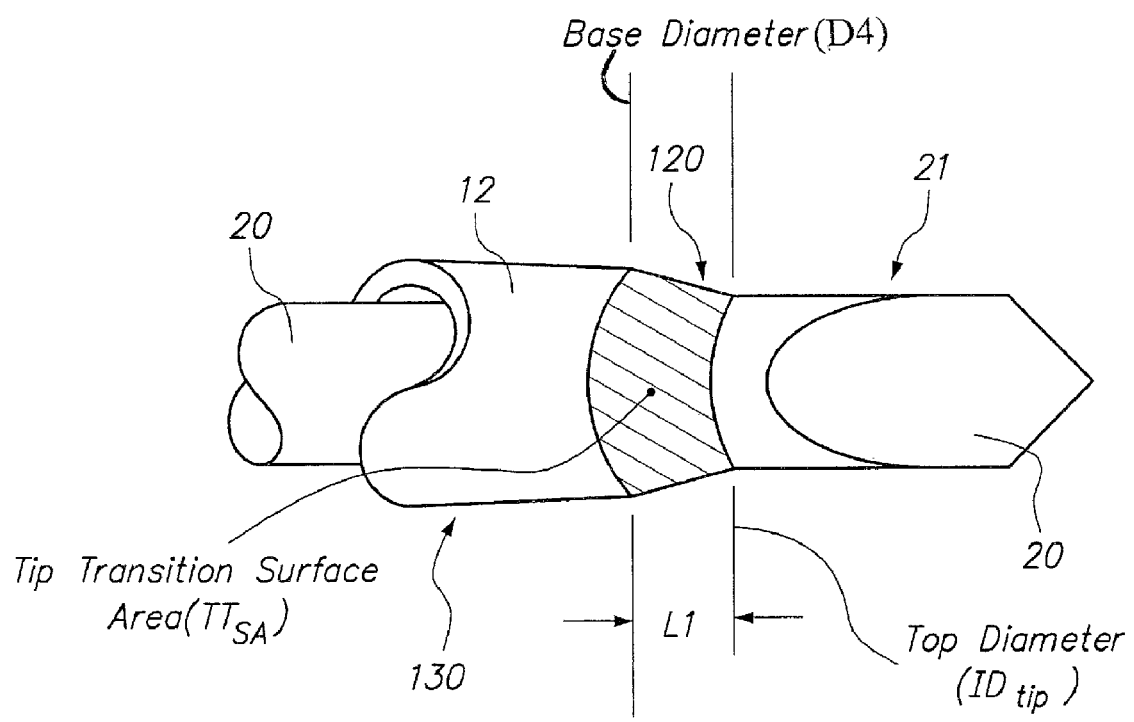
FIG. 4A is a side elevation view of the tip transition region of the needle of FIG. 4.

As shown in FIGS. 4 and 4a, the surface area ($TT_{sa}$) of the frustoconical tip transition region 120 can be calculated using the values of the top radius, base radius and the height of the section and in FIG. 4, the top radius is the radius of the needle 90 at the tip (ID tip/2), the base radius is the radius of the needle at the base of the frustrum (D4/2), and the height of the truncated cone (distal region 120) is the measurement L1. The lateral or outer surface 122 of the frustrum not including the area of the base or the top is the area of interest since the base surface area is not exposed to the bone and the top base is not exposed since the stylet extends through that region.

The applicant has discovered that there is a correlation or relationship between the tip transition surface area ($TT_{sa}$) and the force required for needle penetration. However, there are other parameters that also contribute to determining the required penetration force, such as the angle α2 of the surface area relative to the axial dimension of the needle; the density of the material being penetrated and the distance p of the needle penetration. In any event, the applicant has realized that the force F required for needle penetration is a function of the tip transition surface area ($TT_{sa}$). The angle of the lateral surface area of the tip transition portion (distal region) 120 of the needle 10 relative to the longitudinal axis of the needle 90 is determined by the variables D4 (the diameter shown in FIG. 4A which represents the diameter of the outer cannula 12 at the transition point between the distal and second regions 120, 130), the inner diameter of the distal tip ($ID_{tip}$) and L1. The force F also may change with the depth of needle penetration into a substance p and will also be dependent on the density, dn, of the biopsied material which is not necessarily uniform in nature. The penetration force can thus be expressed in the following manner and is a function of the previously enumerated variables and can be described by the formula: $F=f(TT_{sa}, \alpha 2, p, dn)$.

The applicant has discovered that even relatively small differences in the forward surface area of the needle, namely, the tip transition surface area ($TT_{sa}$) can have a substantial impact on the ability of the needle 90 to penetrate dense material.

Understanding the differences in tip geometry between a sharp and dull piercing tool help assist in appreciating the details and advantages offered by the present invention. It does not take much change in the "sharpness" of the tip of a piercing device to make a sharp device less effective in penetrating material. In other words, the penetrating device's tip can become slightly less sharp or blunt with continued use, which can result in a significant decrease in the device's ability to pierce the material. The difference in the forward surface area of the tip (i.e., the tip transition surface area) between a "sharp" device and a "dull" device may be fairly minimal in terms of total surface area. The applicant has discovered that increases in the tip transition surface area of snarecoil needles whose tip design includes geometric design changes required by the incorporation of the snarecoil at the tip, or the forward surface area of the snarecoil needle tip, translates into the requirement for the application of increased force to penetrate material and the perception that the needle or device is "dull".

The applicant observed that when comparing the performance of different needle designs, there is a correlation between the tip transition surface area ($TT_{sa}$) and the performance of the needle in terms of the force required to penetrate a dense material. The applicant has also discovered that there is a relationship between the inner and outer tube wall thicknesses and the lateral surface area ($TT_{sa}$) of the tip transition region (distal region) 120 and that this relationship helps to determine the performance of the needle 10 by influencing the forces that are required to penetrate dense materials, such as bone.

In accordance with the present invention, the applicant has additionally discovered that there is relationship between the tip transition surface area ($TT_{sa}$) and the cross-sectional area of the needle 90 at the interface between the distal region 120 and the second region 130. The circular area transecting the needle 90 perpendicular to its longitudinal axis at the region where the tip transition region 120 meets the more proximal tip taper defined by the second region 130 is described by the radius D4/2 and is referred to herein as value Ba. The area of this circular region is actually the area of the base of the truncated cone or frustum that is described by the distal region 120. The applicant has discovered that the ratio of ($TT_{sa}$) to Ba is approximately 1 for the needles that offer improved performance in terms of their ease of insertion into dense materials, such as bone, and into the bone marrow spaces. This ratio can be referred to as ratio "A". In words the ratio $A=(TT_{sa})/Ba$. The applicant has discovered that needles that have a ratio A close to or about 1 require relatively smaller forces for needle penetration. In one embodiment, the ratio A is less than 1.2, and preferably equal to or less than 1.1 and more preferably approximately 1.

The applicant has therefore uncovered the concept that needles whose ($TT_{sa}$)/Ba is close to 1 require less force to penetrate dense material, such as bone. The parameter ($TT_{sa}$)/Ba is predictive of penetration force requirements for needles of a specific gauge with those having values closer to 1 requiring less force to penetrate dense materials. More particularly, minimizing the ratio ($TT_{sa}$)/Ba is particularly important to the design of snarecoil biopsy needles manufactured with a "tube within a tube" needle tip (such as outer cannula 12 and inner tube 14) since the greater wall thickness contributed by the double tube (two cannula) design tends to increase the tip transition surface area ($TT_{sa}$).

The applicant believes that the tip transition surface area ($TT_{sa}$) should be approximately equal to the "cross-sectional area" of the needle (described above as the value Ba) for needles to have more optimal penetration characteristics. Intuitively, if the tip transition surface area is larger than the needle cross-sectional area, the geometry of the needle tip is represented by a distal forward surface area that is greater than the cross-sectional area of the needle itself (which would be interpreted as a virtual "bulge" sitting at the needle's tip).

If one were to "deform" the surface area of the tip transition area into another theoretical cross-sectional area in the form of a disc at the end of the needle, the ratio can be understood more intuitively. If this "deformed" cross-sectional tip transition surface area (disc) is significantly larger than the cross-sectional area of the needle, the tip of the needle would have a virtual diameter greater than the diameter of the needle itself which would corresponds to a needle design structure that would impedes forward needle penetration.

In one embodiment, the needle 90 has a tip transition surface area ($TT_{sa}$) that is between about 0.15 and 0.18 square inch. In another embodiment, the tip transition surface area ($TT_{sa}$) is between about 0.17 and 0.20 square inch for 8 gauge needles with optimized TTsa. For example, it has been found that 8 gauge needles that have a tip transition surface area ($TT_{sa}$) of 0.017 in$^2$ compared to 0.0239 in$^2$ appear to require less force to penetrate bone, are technically more acceptable to the user, and are perceived as a better performing needle since it is easier for the user to insert the needle for retrieval of the specimen. While this difference in surface area may appear small, it represents a 40% difference and in the field, users of the respective devices have focused on how much easier it is to operate the device with the smaller tip transition surface area.

It will be appreciated that the present invention is directed to improvements to snarecoil biopsy needle design and in particular, the ease of use of the device is significantly improved by configuring and shaping the outer cannula 12 so that less force is required to insert the needle into and through dense material, such as bone.

Figure 5:
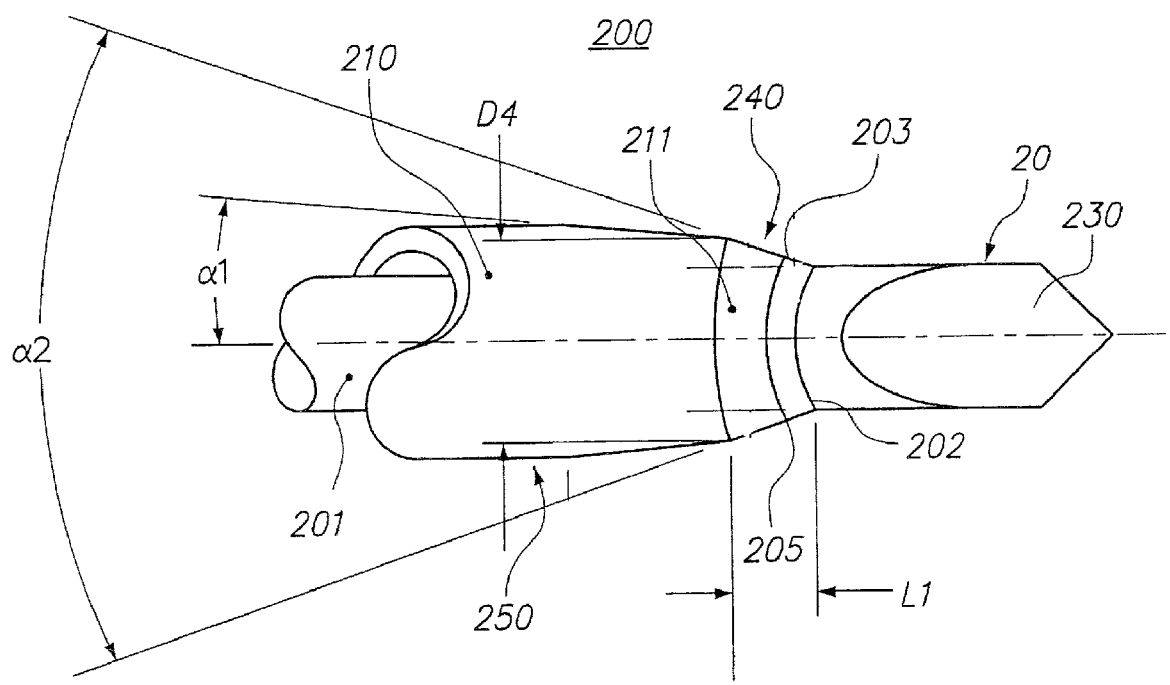
FIG. 5 is a side elevation view of a portion of a needle having an outer cannula and inner cannula according to another embodiment of the present invention.

FIG. 5 illustrates a needle 200 (snarecoil type) that includes an inner cannula 201, outer cannula 210 and a snare (not shown) that is coupled between the two in the same manner described above with reference to tie other needle designs. Stylet 20 is shown in an extended position where the distal end of the stylet 20 protrudes beyond the distal end 202 of the needle 200.

In this embodiment, the distal end 202 of the needle 200 is actually a distalmost section 203 of the inner tube 201 that is exposed when a section of the outer cannula 210 is removed. For example, the distal end of the outer cannula 210 can be removed by a grinding process so as to reduce the outer cannula 210 to a length that exposes the distalmost section 203 of the inner tube 201. This exposed distalmost section 203 of the inner tube 201 can be thought of as being an exposed cutting lip of the inner cannula 201.

The stylet 20 includes a distal end region 230 that extends beyond the distal end of the cannula 210. Similar to the needle 90, the needle 200 includes a distal tip region 240 (similar to region 120) and a second region 250 that is a portion of the body region of the outer cannula 210. However in the embodiment illustrated in FIG. 5, the distal tip region 240 which is characterized as being the tip transition region is actually formed of the distalmost section 203 of the inner tube 201 (which represents the distalmost section of the needle 200) and the distalmost section 211 of the outer cannula 210 after the outer cannula 210 has been subjected to a length modification process, such as a grinding of the distal tip of the outer cannula 210. In other words, in this embodiment, the tip transition region 240 can be seen to be divided into a more proximal component 211 and more distal component 203 by a curvilinear line 205 which separates the more proximal portion 211, which is the distalmost aspect of the outer cannula (tube) 210 from a more distal aspect 203, which is the most distal portion of the exposed inner cannula (tube) 201.

Once again, the second region 250 is a region of the outer tube 210 that has a slight taper albeit much less of a taper than the taper of the tip transition region 240.

It will also be appreciated that the tip transition region (e.g., region 240) can be defined, in another embodiment, entirely by the exposed section 203 of the inner tube 201. In other words, the frustoconical section is defined entirely by the exposed section 203 of the inner tube 201 as by grinding down a length of the outer tube 210 or manufacturing the outer tube 210 to have a specific complementary shape or by connecting the two in a certain manner. The remaining distal section of the outer tube 210 defines the second region 250 where the degree of taper is significantly less than in the tip transition region 240. The inner tube 201 in this embodiment can have an "arrow" shape in that it has a tubular body with a preformed conical shaped distal end section. The base of the conically shaped distal end section has an outer diameter that is approximately equal to the outer diameter of the outer tube at its distal end so as to provide a substantially smooth transition from the conical shaped distal end section to the outer surface of the outer tube. The second region is thus the distal end section of the outer tube that has a slight taper. The "cross-sectional area" of the needle (described above as the value Ba) is defined at the interface between the base of the conical shaped distal end section of the inner tube and the distal end of the outer tube that abuts the base.

It will be understood that FIGS. 4 and 5 merely illustrate that the outer cannula of the biopsy needle can have different shapes and that individual regions of the outer cannula have different surface characteristics, such as an outer surface area and that the tip transition region can be defined not only by the outer surface of the outer tube but can also be defined by a combination of the outer surfaces of the inner tube and outer tube. The relative shapes and dimensions illustrated for these regions are merely for illustrative purposes and are not limiting of the present invention. It will therefore be appreciated that the degree of taper and the relative dimensions of the outer cannula of a needle in accordance with the present invention should be carefully selected based on the teachings herein so that the ratio A which is defined as ($TT_{sa}$)/Ba is equal to or less than 1.2 for 8 gauge needle and preferably is approximately 1 and the ratio A for an 11 gauge needle should be less than or equal to 1.4.

While the embodiments shown and described above are fully capable of achieving the objects and advantages of the present invention, it is to be understood that these embodiments are shown and described solely for the purposes of illustration and not for limitation.

What is claimed is:

1. A biopsy needle for removal of tissue from a patient comprising:
   an outer tube having a distal end;
   an inner tube within said outer tube; and
   a snare having a first proximal end connected to the inner tube and a second distal end coupled to the outer tube, the snare contained within the outer tube, wherein the snare has a variable diameter that is controlled by rotation of the inner tube with respect to the outer tube in a prescribed direction resulting in the opening and closing, respectively, of the snare;
   wherein the outer tube has an outer surface that has a first region that terminates in the distal end and is the distalmost section of the outer tube, and a second region adjacent the first region, the first region representing a tip transition region that is defined between the distal end and an interface between the first and second regions, the interface being defined where a degree of taper of the outer tube changes, the tip transition region having a frustoconically shaped outer surface that defines a surface area (A), wherein a circular shaped area (Ba) comprises an area transecting the needle perpendicular to the longitudinal axis of the needle at a location where the first region interfaces with the second region, the interface between the first and second regions representing a base of the frustoconically shaped first region defined by a diameter of the outer tube, wherein a ratio R=(A)/(Ba) is less than or equal to 1.2 for an 8 gauge needle and less than or equal to 1.4 for an 11 gauge needle.

2. The biopsy needle of claim 1, wherein the ratio R is about 1 for the 8 gauge needle or the 11 gauge needle.

3. The biopsy needle of claim 1, wherein the second region has a tapered construction.

4. The biopsy needle of claim 1, wherein an angle $\alpha 2$ that defines the tip transition surface relative to the longitudinal dimension of the outer tube is greater than an angle $\alpha 1$ that defines the needle taper in the second region relative to the longitudinal dimension of the needle.

5. The biopsy needle of claim 1, wherein the length of the first region is less than the length of the second region as measured along the longitudinal axis of the needle.

6. The biopsy needle of claim 1, wherein the interface between the first and second regions is defined by a substantial change in the taper of the needle toward the proximal end.

7. The biopsy needle of claim 1, wherein the tip transition surface area (A) is between about 0.015 and 0.020 square inch for the 8 gauge needle and between about 0.009 and 0.013 square inch for the 11 gauge needle.

8. The biopsy needle of claim 1, wherein the tip transition surface area (A) is between about 0.017 and 0.018 square inch for the 8 gauge needle.

9. The biopsy needle of claim 1, wherein the snare is integral with the inner tube.

10. The biopsy needle of claim 1, wherein the snare comprises a helical coil.

11. A snare coil type biopsy needle that includes an actuatable snare for removal of tissue from a patient comprising:
an outer tube having a distal end; and
an inner tube disposed partially within said outer tube for actuating the snare, the snare contained within the outer tube;
wherein a distal section of the inner tube extends beyond a distal section of the outer tube and defines the distalmost end of the needle, the needle having a tip transition region that is defined by the distal section of the inner tube and the distal section of the outer tube that is adjacent the distal section of the inner tube that extends beyond the outer tube and defines a distal end of the needle, the outer tube having a second region that is proximal to and adjacent the distal section of the outer tube, wherein the tip transition region, defined by the distal sections of the inner and outer tubes, has a frustoconically shaped outer surface that defines a surface area (A), the tip transition region being located between the distal end of the needle and an interface between the distal section of the outer tube and the second region of the outer tube, wherein a circular shaped area (Ba) comprises an area transecting the needle perpendicular to the longitudinal axis of the needle at a location where the distal section of the outer tube interfaces with the second region, the interface being defined where a degree of taper of the outer tube changes, the interface further representing a base of the frustoconically shaped tip transition region defined by a diameter of the outer tube and wherein a ratio R=(A)/(Ba) is approximately 1 for an 8 gauge needle and is approximately 1.2 for an 11 gauge needle.

12. The biopsy needle of claim 11, wherein each of the tip transition region and the second region has a tapered construction.

13. The biopsy needle of claim 12, wherein the tapered construction is defined by an outward taper in a proximal direction, the degree of outward taper in the tip transition region being greater than the degree of taper in the second region.

14. The biopsy needle of claim 11, wherein the tip transition surface area (A) is between about 0.15 and 0.20 square inch for the 8 gauge needle and between about 0.009 and 0.013 square inch for the 11 gauge needle.

15. The biopsy needle of claim 11, wherein the tip transition surface area (A) is between about 0.17 and 0.18 square inch for the 8 gauge needle.

16. The needle of claim 11, wherein in the tip transition region an outer surface of the distal section of the inner tube transitions to an outer surface of the distal section of the outer tube in a smooth continuous manner.

* * * * *